US006605718B2

United States Patent
Ikeda et al.

(10) Patent No.: US 6,605,718 B2
(45) Date of Patent: Aug. 12, 2003

(54) METHOD FOR REDUCING ORGANIC SOLVENTS REMAINING IN TRIS-(2,3-EPOXYPROPYL)-ISOCYANURATE CRYSTALS

(75) Inventors: Hisao Ikeda, Chiba (JP); Yasuhiro Gunji, Chiba (JP); Motohiko Hidaka, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/790,818

(22) Filed: Feb. 23, 2001

(65) Prior Publication Data
US 2001/0018517 A1 Aug. 30, 2001

(30) Foreign Application Priority Data

Feb. 24, 2000 (JP) .................... 2000-047110

(51) Int. Cl.$^7$ ............................ C07D 251/30
(52) U.S. Cl. .................................... 544/221
(58) Field of Search ........................ 544/221

(56) References Cited

U.S. PATENT DOCUMENTS

| 3,785,385 | A | * | 1/1974 | Johnson ................. 131/140 P |
| 3,953,615 | A | * | 4/1976 | Gupta et al. ................ 426/594 |
| 5,378,786 | A | * | 1/1995 | Ubu et al. ................ 526/344.2 |
| 5,403,365 | A | * | 4/1995 | Merriam et al. .............. 44/621 |
| 6,111,104 | A | * | 8/2000 | Ikeda et al. ................. 544/221 |
| 6,124,454 | A | * | 9/2000 | Ikeda et al. ................. 544/221 |

OTHER PUBLICATIONS

Price, H.P. et al, J. Org. Chem., 32, 1967, 2005–2006.*

* cited by examiner

Primary Examiner—John M. Ford
Assistant Examiner—Thomas McKenzie
(74) Attorney, Agent, or Firm—Oblon, Spivak, McClelland, Maier & Neustadt, P.C.

(57) ABSTRACT

A method for reducing organic solvents remaining in tris-(2,3-epoxypropyl)-isocyanurate crystals, which comprises pulverizing, as a material, crystal particles of tris-(2,3-epoxypropyl)-isocyanurate obtained by a recrystallization method, while evaporating a volatile component from the surface of the particles.

23 Claims, No Drawings

METHOD FOR REDUCING ORGANIC SOLVENTS REMAINING IN TRIS-(2,3-EPOXYPROPYL)-ISOCYANURATE CRYSTALS

BACKGROUND OF THE INVENTION

1. Field of the Invention

The present invention relates to a method for reducing organic solvents remaining in tris-(2,3-epoxypropyl)-isocyanurate crystals, by removing the organic solvents remaining in said crystals while evaporating a volatile component from the surface of the crystals, particularly by e.g. machine pulverization in a gas stream.

2. Discussion of Background

In view of an increasing demand in recent years for the properties required for a solder resist material, such as adhesion, electrical insulating properties, soldering heat resistance and solvent resistance, a solder resist ink composition is presently used which is a combination of a photosensitive prepolymer and a thermosetting resin. Namely, it is designed to satisfy the above required properties by forming a solder resist pattern by the photosensitive prepolymer, followed by thermosetting. Further, demands have been increasing for high densification of printed circuit boards along with a trend for light weight and miniaturization of electronic appliances in recent years, for low scumming during formation of solder resist patterns for surface mounting of parts and for precision in embedding between circuits. Accordingly, as the thermosetting resin to be incorporated to the solder resist ink, a fine particulate solid epoxy having high solvent resistance is desired.

As a solid epoxy to satisfy the above required properties, tris-(2,3-epoxypropyl)-isocyanurate may be mentioned. Tris-(2,3-epoxypropyl)-isocyanurate has three asymmetric carbon atoms, and crystals made of an equimolar mixture of (2R,2'R,2"R)-tris-(2,3-epoxypropyl)-isocyanurate and (2S,2'S,2"S)-tris-(2,3-epoxypropyl)-isocyanurate, wherein all of the three asymmetric carbon atoms are optically isotropic, are commonly called β-form crystals and known to give crystals having a high melting point of a level of about 150° C. This is attributable to the fact that a pair of these two types of enantiomers form a molecular lattice having six firm hydrogen bonds and thus form a crystal lattice. On the other hand, crystals made of a mixture of (2R,2R,2S)-tris-(2,3-epoxypropyl)-isocyanurate and (2S,2S,2R)-tris-(2,3-epoxypropyl)-isocyanurate, wherein one of the three asymmetric carbon atoms is different in the optical anisotropy, are commonly called α-form crystals, and they do not have the above crystal structure and accordingly present only a low melting point of a level of about 100° C. The β-form tris-(2,3-epoxypropyl)-isocyanurate crystals not only have a high melting point but also have an extremely low solubility in various solvents. Accordingly, when they are used as a crosslinking agent for different types of compounds or for reactive polymers in the form of a one pack type reactive mixture, the reaction will not proceed during storage, until they are forcibly cured. Such β-form crystals have been used for applications to electric and electronic materials, for example, as a solder resist ink composition of photocuring/thermosetting combined type.

The liquid epoxy composition is likely to undergo an increase in viscosity during storage, since a part of the epoxy compound dissolves in the solvent, and entanglement with the photosensitive prepolymer is likely to result, whereby elution tends to be poor during washing off of the non-exposed portion. JP-B-7-17737 discloses use of β-form tris-(2,3-epoxypropyl)-isocyanurate as a hardly soluble epoxy compound. β-form tris-(2,3-epoxypropyl)-isocyanurate fine particles which have a high melting point and which are hardly soluble, are in a state enclosed by a photosensitive prepolymer, whereby they will not reduce the solubility of the photosensitive prepolymer at the non-exposed portion. Further, they are hardly soluble in an organic solvent, whereby the exposed portion is hardly eroded by a developer, whereby there will be no deterioration in the sensitivity. Further, the storage stability of the solder resist ink composition is excellent.

As a method for separating β-form tris-(2,3-epoxypropyl)-isocyanurate and α-form tris-(2,3-epoxypropyl)-isocyanurate from tris-(2,3-epoxypropyl)-isocyanurate, a separation method has been available wherein a solvent which dissolves α-form tris-(2,3-epoxypropyl)-isocyanurate relatively well and which hardly dissolves β-form tris-(2,3-epoxypropyl)-isocyanurate, for example, an alcohol such as methanol, is employed. For example, Journal of Thermal Analysis, vol.36 (1990) p.1819 discloses separation by means of a methanol solvent. Further, Plaste und Kautschuk 23 Jahrgang Heft 4/1975 discloses a method wherein firstly a methanol solvent is used for separating β-form tris-(2,3-epoxypropyl)-isocyanurate, and then the β-form tris-(2,3-epoxypropyl)-isocyanurate is purified by chloroform. Further, Kobunshi Ronbunshu (polymer report collection), vol.47, No.3 (1990) p.169, discloses a method wherein synthesized tris-(2,3-epoxypropyl)-isocyanurate is put into methanol, followed by heating and stirring, whereupon the non-dissolved content is collected by filtration, and the obtained non-dissolved substance is re-crystallized from methyl ethyl ketone to obtain β-form tris-(2,3-epoxypropyl)-isocyanurate crystals.

Many of β-form tris-(2,3-epoxypropyl)-isocyanurates obtained by such separation methods, hardly undergo crystal growth, and many of them have a small particle size, whereby the filtration operation in the filtration step tends to be very difficult. Accordingly, it is undesirable that the crystals obtained by recrystallization are too fine.

Further, by a single separation operation by the foregoing separation method, β-form tris-(2,3epoxypropyl)-isocyanurate crystals tend to contain the solvent for recrystallization, chlorine-containing impurities or other impurities. Accordingly, it will be necessary to remove them by further carrying out recrystallization or by melting the crystals once.

Particularly, if the remaining organic solvent is not adequately removed, when the tris-(2,3-epoxypropyl)-isocyanurate is used for e.g. a solder resist material, holes formed by evaporation of the solvent are likely to form on the surface of a printed circuit board, and original properties of the resist material can not be adequately obtained. Further, there may be a problem in an application in which surface smoothness is required. Further, in a case where the remaining organic solvent is a halogenated hydrocarbon, it is not suitable for applications to electronic materials. Further, in a case where the remaining organic solvent is a protic organic solvent, storage stability of a composition may be impaired by proton in some cases.

JP-B-48-24039 discloses a process wherein a chlorohydrin ester of isocyanuric acid obtained by reacting cyanuric acid with epichlorohydrin, is dehydrochlorinated with an alkali, the alkali metal chloride thereby formed is separated, and the obtained epichlorohydrin solution of tris-(2,3-epoxypropyl)-isocyanurate is concentrated to a tris-(2,3- epoxypropyl)-isocyanurate concentration of from 50 to 60%, and then the solution is cooled to from 20 to 25° C. to obtain tris-(2,3-epoxypropyl)-isocyanurate crystals in an yield of 27% based on cyanuric acid. However, the crystals are obtained by crystallization from the epichlorohydrin solution, whereby a large amount of epichlorohydrin, etc. are contained in the interior of the crystals. Further, epichlorohydrin is composed of a hydrolyzable chlorine which is not only hazardous to human bodies but also hazardous to applications to electronic materials, and should be contained as little as possible. However, epichlorohydrin remaining in the crystals can be removed only by heating the crystals to at least the melting point to melt the crystals once. Such a method makes the production step more complicated, and costs much, whereby it is not practical industrially.

SUMMARY OF THE INVENTION

It is an object of the present invention to provide a method to make the amount of organic solvents remaining in tris-(2,3-epoxypropyl)-isocyanurate crystals obtained by a recrystallization method, particularly β-form tris-(2,3-epoxypropyl)-isocyanurate crystals, extremely small.

According to a first aspect of the present invention, there is provided a method for reducing organic solvents remaining in tris-(2,3-epoxypropyl)-isocyanurate crystals, which comprises pulverizing, as a material, crystal particles of tris-(2,3-epoxypropyl)-isocyanurate obtained by a recrystallization method, while evaporating a volatile component from the surface of the particles.

According to a second aspect of the present invention, there is provided the method for reducing the remaining organic solvents, wherein the crystal particles of tris-(2,3-epoxypropyl)-isocyanurate as a material are obtained by reacting cyanuric acid with epichlorohydrin in the presence of a catalyst to form a chlorohydrin ester of isocyanuric acid, followed by dehydrochlorination with an alkali, separating off the resulting alkali metal chloride to obtain a reaction solution containing tris-(2,3-epoxypropyl)-isocyanurate, removing a solvent from the solution to obtain tris-(2,3epoxypropyl)-isocyanurate, and recrystallizing it by means of a solvent.

According to a third aspect of the present invention, there is provided the method for reducing the remaining organic solvents, wherein the recrystallization solvent is selected from the group consisting of acetonitrile, dichloroethane, dioxane, toluene, dimethylformamide, methanol, ethanol and isopropyl alcohol.

According to a fourth aspect of the present invention, there is provided the method for reducing the remaining organic solvents, wherein the pulverization while evaporating a volatile component from the surface of the particles is carried out in a gas stream.

According to a fifth aspect of the present invention, there is provided the method for reducing the remaining organic solvents, wherein the crystal particles are pulverized to an average particle size of from 0.5 to 20 μm.

According to a sixth aspect of the present invention, there is provided the method for reducing the remaining organic solvents, wherein the concentration of the remaining organic solvents is at most 300 ppm.

According to a seventh aspect of the present invention, there is provided the method for reducing the remaining, organic solvents, wherein the crystal particles of tris-(2,3-epoxypropyl)-isocyanurate are crystal particles of β-form tris-(2,3-epoxypropyl)-isocyanurate.

According to a eighth aspect of the present invention, there is provided the method for reducing the remaining organic solvents, wherein the recrystallization solvent is selected from the group consisting of acetonitrile, dichloroethane, dioxane, toluene and dimethylformamide.

According to a ninth aspect of the present invention, there is provided the method for reducing the remaining organic solvents, wherein the remaining organic solvents are epichlorohydrin and acetonitrile.

DETAILED DESCRIPTION OF THE PREFERRED EMBODIMENTS

Now, the present invention will be described in detail with reference to the preferred embodiments.

In the present invention, as the pulverization while evaporating a volatile component from the surface of the particles, a pulverization carried out in a gas stream, or a pulverization carried out under reduced pressure, may be mentioned. The pulverization carried out in a gas stream is particularly effective. Here, the gas stream is a stream of a gas such as air or an inert gas including nitrogen gas and argon gas, and particularly preferred is nitrogen gas.

The pulverization in a gas stream is carried out by using a pulverizer such as 200 AFG Model counter jet mill manufactured by ALPINE or KJ-200 Model cross jet mill manufactured by Kurimoto Ltd. The mechanism of such types of pulverizers is such that a high pressure air or inert gas such as nitrogen is sprayed into the pulverizer together with a sample, and the sample particles are collided with one another and are pulverized. The pressure of the gas is from 1 to 10 kg/cm$^2$. By the gas stream, a volatile component evaporates from the surface of particles which are newly formed by the pulverization, and organic solvents contained in the crystals are reduced. The crystal particles are pulverized to an average particle size of from 0.5 to 20 μm. At this time, the concentration of the organic solvents remaining in the pulverized crystal particles is at most 300 ppm, usually from 100 to 200 ppm.

The crystal particles of tris-(2,3-epoxypropyl)-isocyanurate of the present invention may be any crystals of tris-(2,3-epoxypropyl)-isocyanurate having an average particle size exceeding 20 μm and at most 500 μm. However, tris-(2,3-epoxypropyl)-isocyanurate crystals obtained by a recrystallization method are particularly preferred.

Namely, (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a tri-substituted phosphine and a quaternary phosphonium salt, as a catalyst, are reacted to obtain a reaction solution, from 3 to 6 mols of an alkali metal hydroxide or an alkali metal alcoholate is added to the reaction solution for dehydrochlorination, the resulting alkali metal salt is removed to obtain a reaction solution containing tris-(2,3-epoxypropyl)-isocyanurate, and a solvent is removed to obtain tris-(2,3-epoxypropyl)-isocyanurate.

In the production of the tris-(2,3-epoxypropyl)-isocyanurate crystals, as examples of the catalyst (c), the tertiary amine may, for example, be tripropylamine, tributylamine or N,N'-dimethylpiperazine. The quaternary ammonium salt may, for example, be tetramethylammonium halide, tetraethylammonium halide or tetrabutylammonium halide, wherein the halide may, for example, be chloride, bromide or iodide. The quaternary ammonium base may, for example, be tetramethylammonium hydroxide or benzyltrimethylammonium hydroxide. The tri-substituted phosphine may, for example, be tripropylphosphine, tributylphosphine, triphenylphosphine or tritolylphosphine, and the quaternary phosphonium salt may, for example, be tetramethylphosphonium halide, tetrabutylphosphonium halide, methyltriphenylphosphonium halide or ethyltriphenylphosphonium halide, wherein the halide may, for example, be chloride, bromide or iodide. Among the above-mentioned compounds, a quaternary ammonium salt or a quaternary phosphonium salt is particularly preferred since the reaction proceeds efficiently under a mild condition with no substantial side reaction. Particularly preferred is a quaternary ammonium salt, such as tetramethylammonium halide, tetraethylammonium halide or tetrabutylammonium halide, wherein the halide is chloride or bromide, whereby the side reactions can further be suppressed, and removal of the catalyst after the reaction can easily be made simply by washing with water.

To the reaction solution thus obtained, from 3 to 6 mols of an alkali metal hydroxide or an alkali metal alcoholate is added for dehydrochlorination, and the resulting alkali metal salt is separate off by washing with water or filtration, to obtain a reaction solution containing tris-(2,3-epoxypropyl)-isocyanurate. As such an alkali metal hydroxide, sodium hydroxide, potassium hydroxide or lithium hydroxide may, for example, be mentioned, and as such an alkali metal alcoholate, sodium methylate, sodium ethylate, potassium methylate or potassium ethylate may, for example, be mentioned. The tris-(2,3-epoxypropyl)-isocyanurate thus obtained is a mixture of β-form tris-(2,3-epoxypropyl)-isocyanurate and α-form tris-(2,3-epoxypropyl)-isocyanurate in a weight ratio of 1:3.

The tris-(2,3-epoxypropyl)-isocyanurate thus obtained is subjected to recrystallization from a recrystallization solvent such as acetonitrile, dichloroethane, dioxane, toluene, dimethylformamide, methanol, ethanol or isopropyl alcohol to obtain tris-(2,3-epoxypropyl)-isocyanurate which can be used as a material for the present invention.

In the present invention, the mixture of β-form and α-form tris-(2,3-epoxypropyl)-isocyanurate may be used as a material, but crystal particles of β-form tris-(2,3-epoxypropyl)-isocyanurate are used preferably.

The β-form tris-(2,3-epoxypropyl)-isocyanurate crystals are obtained, for example, by reacting cyanuric acid with epichlorohydrin in the presence of a catalyst to form a chlorohydrin ester of isocyanuric acid, followed by dehydrochlorination with an alkali, separating the resulting alkali metal chloride to obtain a reaction solution containing tris-(2,3-epoxypropyl)-isocyanurate, evaporating a solvent from the reaction solution to obtain tris-(2,3-epoxypropyl)-isocyanurate, and recrystallizing it. Here, the recrystallization solvent may, for example, be acetonitrile, dichloroethane, toluene, dioxane or dimethylformamide, and acetonitrile is particularly preferred.

The recrystallization is carried out by heating the above solvent to a temperature at which tris-(2,3epoxypropyl)-isocyanurate is dissolved therein, and gradually cooling it. The solution may be cooled gradually as it is, or seed crystals may be added thereto for gradual cooling. As the seed crystals, either β-form or α-form tris-(2,3-epoxypropyl)-isocyanurate may be used.

The tris-(2,3-epoxypropyl)-isocyanurate precipitated by recrystallization is collected by filtration such as suction filtration, filter press filtration or centrifugal filtration.

The tris-(2,3-epoxypropyl)-isocyanurate collected by filtration and containing the liquid content contains impurities as components of the liquid content, and it may be washed with an organic solvent. The organic solvent may, for example, be methanol, ethanol, isopropyl alcohol, methyl ethyl ketone, acetonitrile, dimethylformamide or epichlorohydrin.

The remaining organic solvents to be reduced in the present invention are epichlorohydrin as a reaction substrate and the solvent used for the recrystallization.

The β-form tris-(2,3-epoxypropyl)-isocyanurate crystals obtained by the recrystallization have an average particle size of from 10 to 500 μm. Among particles having such a particle size, crystals having an average particle size exceeding 20 μm and at most 500 μm can be used in the present invention.

Even if the β-form tris-(2,3-epoxypropyl)-isocyanurate crystals obtained by such a recrystallization method are dried at a temperature of from room temperature to 90° C. under reduced pressure, the organic solvents remaining in the inside of the crystals are hardly reduced and the amount thereof is usually so high as from 1,000 to 2,000 ppm, thus causing decrease in purity of products and problems for use. In such a case, by drying the crystals at a temperature of from 100 to 140° C., preferably from 120 to 140° C., in a gas stream under normal pressure or under reduced pressure, the remaining organic solvents may be reduced to at most 300 ppm. The above temperature of from 100 to 140° C., preferably from 120 to 140° C., is a temperature of at least the melting point of α-form tris-(2,3epoxypropyl)-isocyanurate and a temperature of less than the melting point of β-form tris-(2,3-epoxypropyl)-isocyanurate. By drying the crystals at this temperature in a gas stream, in the β-form tris-(2,3-epoxypropyl)-isocyanurate crystals containing α-form tris-(2,3epoxypropyl)-isocyanurate in the interior thereof, a part of the α-form tris-(2,3-epoxypropyl)-isocyanurate will be melted and liquefied. Through this liquid portion, epichlorohydrin as an impurity and the organic solvent used for recrystallization will be discharged out of the crystals.

However, in the present invention, the organic solvents remaining in the β-form tris-(2,3-epoxypropyl)-isocyanurate crystals can be reduced by carrying out a step of pulverizing the crystals in a gas stream at room temperature, without a drying step at a temperature of from 100 to 140° C., preferably from 120 to 140° C., which is a temperature of at least the melting point of the α-form tris-(2,3-epoxypropyl)-isocyanurate.

The pulverization is carried out by pulverizing the β-form tris-(2,3-epoxypropyl)-isocyanurate crystals to an average particle size of from 0.5 to 20 μm. By the pulverization, the remaining organic solvents can be reduced to at most 300 ppm.

The average particle size and the particle size distribution of the pulverized product can be controlled by pulverization conditions or a classifying rotor. When the β-form tris-(2,3-epoxypropyl)-isocyanurate crystals are pulverized to an average particle size of from 0.5 to 20 μm, the organic solvents in the interior of the crystals can effectively be removed. The smaller the average particle size of the pulverized crystals, the higher the removal ratio of the solvents. However, if the average particle size is much smaller than this range, the pulverization efficiency tends to be low. Further, if the average particle size is at least 20 μm, the removal ratio of the solvents tends to be low.

As the gas stream during pulverization, air or an inert gas may be used, but preferred is an inert gas such as nitrogen gas so as to avoid risks of dust explosion in a case of pulverizing an organic substance having a volume resistivity of so high as $2 \times 10^{13}$ Ω.cm such as tris-(2,3-epoxypropyl)-isocyanurate.

The preferred volume of the gas stream based on the amount of a sample supplied depends on the shape of an apparatus or the pressure of the gas stream, but it is preferred to use from 5 to 40 Nm$^3$ of nitrogen per kg of a sample in a case of conducting pulverization by means of 200 AFG Model counter jet mill manufactured by ALPINE under a nitrogen pressure of 6 kg/cm$^2$. If it is smaller than this range, the effect of reducing the solvents tends to decrease, and if it is larger than the above range, the removal effect will not increase in proportion to the volume of nitrogen used. However, the larger the volume of nitrogen, the more easily the solvents can be removed on the whole, and the risks of dust explosion tend to decrease since the dust concentration tends to decrease.

In the pulverization method using such a huge amount of nitrogen, it is common to recycle the stream of nitrogen used so as to save the cost of nitrogen. However, in a case where the gas stream of nitrogen is recycled for a long period of time, the vapor concentration of organic solvents in the gas stream of nitrogen gradually increases, whereby evaporation of the organic solvents from the surface of particles tends to be impaired. It is possible to trap the organic solvent by cooling the recovered gas in a case where the solvent has a high boiling point, but as an effective method, the gas stream of nitrogen may be discharged at a constant discharge rate, and nitrogen gas may be anew supplied to make up for the discharged volume to prevent accumulation of the vapor concentration of the solvents in the gas stream. The volume of the nitrogen gas discharged is preferably from about 2 to about 20 vol % of the total nitrogen gas introduced per unit sample, i.e. from 0.1 to 8 Nm$^3$ per kg of the sample.

Method for Quantitative Analysis of Organic Solvents Remaining in the Crystals

The organic solvent remaining in the crystals is determined in such a manner that to a sample (crystals), 20 times of an organic solvent other than the solvent to be determined, such as dimethylformamide or acetonitrile, is added and dissolved by heating to 80° C., followed by quantitative analysis by gas chromatography.

Now, the present invention will be described in further detail with reference to Examples. However, it should be understood that the present invention is by no means restricted to such specific Examples.

Production Example 1 of β-form tris-(2,3-epoxypropyl)-isocyanurate Crystals by a Recrystallization Method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using acetonitrile as a recrystallization solvent will be described below.

Into a flask equipped with a stirrer and a thermometer, 1,000 g of the obtained tris-(2,3epoxypropyl)-isocyanurate and 1,000 g of acetonitrile were added and dissolved at 57° C. with stirring, followed by cooling to 50° C., and 7 g of β-form tris-(2,3epoxypropyl)-isocyanurate was added thereto as seed crystals. Then, the solution was cooled to 14° C. over a period of 4 hours and subjected to suction filtration, and the resulting cake was successively washed with 300 g of methanol. The obtained cake was dried under reduced pressure at 80° C. for 4 hours. After the drying, 182 g of β-form tris-(2,3-epoxypropyl)-isocyanurate crystals having a melting point of from 150 to 156° C., an epoxy equivalent of 101 g/eq, 150 ppm of hydrolyzable chlorine and an average particle size of 75 µm, containing 50 ppm of epichlorohydrin and 1,360 ppm of acetonitrile remaining in the interior of the crystals, were obtained.

Production Example 2 of β-form tris-(2,3-epoxypropyl)-isocyanurate Crystals by a Recrystallization Method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using toluene as a recrystallization solvent will be described below.

Into a flask equipped with a stirrer and a thermometer, 1,000 g of the obtained tris-(2,3epoxypropyl)-isocyanurate and 4,000 g of toluene were added and dissolved at 110° C. with stirring. The solution was cooled to 65° C. over a period of 3 hours and subjected to suction filtration, and the resulting cake was successively washed with 300 g of methanol. The obtained cake was dried under reduced pressure at 80° C. for 4 hours. After the drying, 188 g of β-form tris-(2,3epoxypropyl)-isocyanurate crystals having a melting point of from 150 to 155° C., an epoxy equivalent of 102 g/eq, 260 ppm of hydrolyzable chlorine and an average particle size of 45 µm, containing 50 ppm of epichlorohydrin and 1,520 ppm of toluene remaining in the interior of the crystals, were obtained.

Production Example 3 of β-form tris-(2,3-epoxypropyl)-isocyanurate Crystals by a Recrystallization Method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using dioxane as a recrystallization solvent will be described below.

Into a flask equipped with a stirrer and a thermometer, 1,000 g of the obtained tris-(2,3-epoxypropyl)-isocyanurate and 1,000 g of dioxane were added and dissolved at 75° C. with stirring, followed by cooling to 65° C., and 7 g of β-form tris-(2,3epoxypropyl)-isocyanurate was added thereto as seed crystals. Then, the solution was cooled to 30° C. over a period of 4 hours and subjected to suction filtration, and the resulting cake was successively washed with 300 g of methanol. The obtained cake was dried under reduced pressure at 80° C. for 4 hours. After the drying, 185 g of β-form tris-(2,3-epoxypropyl)-isocyanurate crystals having a melting point of from 150 to 155° C., an epoxy equivalent of 101 g/eq, 250 ppm of hydrolyzable chlorine and an average particle size of 60 μm, containing 50 ppm of epichlorohydrin and 1,460 ppm of dioxane remaining in the interior of the crystals, were obtained.

Production Example 4 of β-form tris-(2,3-epoxypropyl)-isocyanurate Crystals by a Recrystallization Method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using dimethylformamide as a recrystallization solvent will be described below.

Into a flask equipped with a stirrer and a thermometer, 1,000 g of the obtained tris-(2,3-epoxypropyl)-isocyanurate and 1,000 g of dimethylformamide were added and dissolved at 65° C. with stirring, followed by cooling to 55° C., and 5 g of β-form tris-(2,3-epoxypropyl)-isocyanurate was added thereto as seed crystals. Then, the solution was cooled to 20° C. over a period of 4 hours and subjected to suction filtration, and the resulting cake was successively washed with 300 g of methanol. The obtained cake was dried under reduced pressure at 80° C. for 4 hours. After the drying, 162 g of β-form tris-(2,3-epoxypropyl)-isocyanurate crystals having a melting point of from 150 to 154° C., an epoxy equivalent of 101 g/eq, 200 ppm of hydrolyzable chlorine and an average particle size of 50 μm, containing 50 ppm of epichlorohydrin and 1,800 ppm of dimethylformamide remaining in the interior of the crystals, were obtained.

Production Example 5 of β-form tris-(2,3-epoxypropyl)-isocyanurate crystals by a recrystallization method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using 1,2-dichloroethane as a recrystallization solvent will be described below.

Into a flask equipped with a stirrer and a thermometer, 1,000 g of the obtained tris-(2,3-epoxypropyl)-isocyanurate and 1,500 g of 1,2-dichloroethane were added and dissolved at 73° C. with stirring. The solution was cooled to 25° C. over a period of 6 hours and subjected to suction filtration, and the resulting cake was successively washed with 300 g of methanol. The obtained cake was dried under reduced pressure at 80° C. for 4 hours. After the drying, 165 g of β-form tris-(2,3-epoxypropyl)-isocyanurate crystals having a melting point of from 150 to 154° C., an epoxy equivalent of 101 g/eq, 220 ppm of hydrolyzable chlorine and an average particle size of 50 μm, containing 50 ppm of epichlorohydrin and 1,400 ppm of 1,2-dichloroethane remaining in the interior of the crystals, were obtained.

Production Example 6 of tris-(2,3-epoxypropyl)-isocyanurate Crystals by a Recrystallization Method Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out a reaction. Then, the temperature of the reaction system was lowered to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, 3,600 g of water was added so that the formed sodium chloride was dissolved therein and washed out, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Then, epichlorohydrin in the epichlorohydrin solution of tris-(2,3-epoxypropyl)-isocyanurate obtained by washing with water was distilled off to obtain 1,604 g of tris-(2,3-epoxypropyl)-isocyanurate having an epoxy equivalent of 105 g/eq. A method of recrystallizing said tris-(2,3-epoxypropyl)-isocyanurate using methanol as a recrystallization solvent will be described below.

Into a flask equipped with a stirrer and a thermometer, 1,000 g of the obtained tris-(2,3-epoxypropyl)-isocyanurate and 4,000 g of methanol were added and dissolved at 60° C. with stirring. The solution was cooled to 10° C. over a period of 6 hours and subjected to suction filtration, and the resulting cake was successively washed with 300 g of methanol. The obtained cake was dried under reduced pressure at 80° C. for 4 hours. After the drying, 820 g of tris-(2,3-epoxypropyl)-isocyanurate crystals having a melting point of from 101 to 110° C., an epoxy equivalent of 100 g/eq, 800 ppm of hydrolyzable chlorine and an average particle size of 30 $\mu$m, containing 80 ppm of epichlorohydrin and 1,300 ppm of methanol remaining in the interior of the crystals, were obtained.

EXAMPLE 1

The β-form tris-(2,3-epoxypropyl)-isocyanurate crystals obtained by a recrystallization method in Production Example 1 were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 50 ppm to 20 ppm, and the remaining acetonitrile was reduced from 1,360 ppm to 170 ppm.

EXAMPLE 2

The β-form tris-(2,3-epoxypropyl)-isocyanurate crystals obtained by a recrystallization method in Production Example 2 were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 50 ppm to 20 ppm, and the remaining toluene was reduced from 1,520 ppm to 200 ppm.

EXAMPLE 3

The β-form tris-(2,3-epoxypropyl)-isocyanurate crystals obtained by a recrystallization method in Production Example 3 were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 50 ppm to 20 ppm, and the remaining dioxane was reduced from 1,460 ppm to 210 ppm.

EXAMPLE 4

The β-form tris-(2,3-epoxypropyl)-isocyanurate crystals obtained by a recrystallization method in Production Example 4 were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 50 ppm to 20 ppm, and the remaining dimethylformamide was reduced from 1,800 ppm to 250 ppm.

EXAMPLE 5

The β-form tris-(2,3-epoxypropyl)-isocyanurate crystals obtained by a recrystallization method in Production Example 5 were pulverized by 200 AFG Model counter jet mill manufactured by ALPINE. The pulverization was carried out under a nitrogen pressure of 6.0 kg/cm$^2$, with a nitrogen amount of 400 Nm$^3$ /h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 50 ppm to 20 ppm, and the remaining 1,2-dichloroethane was reduced from 1,400 ppm to 180 ppm.

EXAMPLE 6

The tris-(2,3-epoxypropyl)-isocyanurate crystals obtained by a recrystallization method in Production Example 6 were pulverized by 200 AFG Model counter jet mill manufactured by ALPINE. The pulverization was carried out under a nitrogen pressure of 6.0 kg/cm$^2$, with a nitrogen amount of 400 Nm$^3$/h, with a sample-supplying rate of 40 kg/h, and with a classifying rotor rotated at 5,000 rpm. By the pulverization and classification, the crystals were pulverized to fine particles having an average particle size of 3.0 $\mu$m, and the remaining epichlorohydrin was reduced from 80 ppm to 30 ppm, and the remaining methanol was reduced from 1,300 ppm to 150 ppm.

EXAMPLE 7

The β-form tris-(2,3-epoxypropyl)-isocyanurate crystals obtained in Production Example 1 were pulverized by 200

AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 50 ppm to 15 ppm, and the remaining acetonitrile was reduced from 1,360 ppm to 80 ppm.

EXAMPLE 8

The β-form tris-(2,3-epoxypropyl)-isocyanurate crystals obtained in Production Example 2 were pulverized by 200 AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 50 ppm to 15 ppm, and the remaining toluene was reduced from 1,520 ppm to 100 ppm.

EXAMPLE 9

The β-form tris-(2,3-epoxypropyl)-isocyanurate crystals obtained in Production Example 3 were pulverized by 200 AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 50 ppm to 15 ppm, and the remaining dioxane was reduced from 1,460 ppm to 110 ppm.

EXAMPLE 10

The β-form tris-(2,3-epoxypropyl)-isocyanurate crystals obtained in Production Example 4 were pulverized by 200 AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 50 ppm to 15 ppm, and the remaining dimethylformamide was reduced from 1,800 ppm to 200 ppm.

EXAMPLE 11

The β-form tris-(2,3-epoxypropyl)-isocyanurate crystals obtained in Production Example 5 were pulverized by 200 AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 50 ppm to 15 ppm, and the remaining 1,2-dichloroethane was reduced from 1,400 ppm to 90 ppm.

EXAMPLE 12

The tris-(2,3-epoxypropyl)-isocyanurate crystals obtained in Production Example 6 were pulverized by 200 AFG Model counter jet mill manufactured by ALPINE. The pulverization was carried out under a nitrogen pressure of 6.0 kg/cm$^2$, with a nitrogen amount of 800 Nm$^3$/h, with a sample-supplying rate of 30 kg/h, and with a classifying rotor rotated at 12,000 rpm. By the pulverization, the crystals were pulverized to fine particles having an average particle size of 1.5 μm, and the remaining epichlorohydrin was reduced from 80 ppm to 20 ppm, and the remaining methanol was reduced from 1,300 ppm to 70 ppm.

EXAMPLE 13

The β-form tris-(2,3-epoxypropyl)-isocyanurate crystals obtained by a recrystallization method in Production Example 1 were pulverized by 200 AFG Model counter jet mill manufactured by ALPINE. The pulverization was carried out under a nitrogen pressure of 6.0 kg/cm$^2$, with a nitrogen amount of 200 Nm$^3$/h, with a sample-supplying rate of 60 kg/h, and with a classifying rotor rotated at 5,000 rpm. By the pulverization and classification, the crystals were pulverized to fine particles having an average particle size of 20 μm, and the remaining epichlorohydrin was reduced from 50 ppm to 30 ppm, and the remaining acetonitrile was reduced from 1,360 ppm to 850 ppm.

EXAMPLE 14

The β-form tris-(2,3-epoxypropyl)-isocyanurate crystals obtained by a recrystallization method in Production Example 5 were pulverized by 200 AFG Model counter jet mill manufactured by ALPINE. The pulverization was carried out under a nitrogen pressure of 6.0 kg/cm$^2$, with a nitrogen amount of 200 Nm$^3$/h, with a sample-supplying rate of 60 kg/h, and with a classifying rotor rotated at 5,000 rpm. By the pulverization and classification, the crystals were pulverized to fine particles having an average particle size of 18 μm, and the remaining epichlorohydrin was reduced from 50 ppm to 35 ppm, and the remaining 1,2-dichloroethane was reduced from 1,400 ppm to 900 ppm.

By the present invention, organic solvents remaining in tris-(2,3-epoxypropyl)-isocyanurate crystals can be removed by pulverizing crystal particles of tris-(2,3-epoxypropyl)-isocyanurate obtained by a recrystallization method to an average particle size of from 0.5 to 20 μm, while evaporating a volatile component from the surface of the particles.

With respect to tris-(2,3-epoxypropyl)-isocyanurate crystals obtained by a conventional recrystallization method, the remaining organic solvents involved in the interior of the crystals have been removed by heating the crystals to a temperature of at least the melting point of tris-(2,3-epoxypropyl)-isocyanurate. For β-form tris-(2,3-epoxypropyl)-isocyanurate crystals, heating at a temperature of at least 150° C. has been necessary.

Further, in a method for precipitating β-form tris-(2,3-epoxypropyl)-isocyanurate crystals containing α-form tris-(2,3-epoxypropyl)-isocyanurate from a reaction solution containing tris-(2,3-epoxypropyl)-isocyanurate, organic solvents (epichlorohydrin and an organic solvent used for recrystallization) may be removed in such a manner that the crystals are heated to a temperature of from 100 to 140° C., preferably from 120 to 140° C., to melt α-form tris-(2,3-epoxypropyl)-isocyanurate in said crystals, and through this melted portion in the crystals, the organic solvents are removed. However, in the present invention, the organic solvents can be removed only by pulverizing the tris-(2,3-epoxypropyl)-isocyanurate crystals obtained by a recrystallization method in a gas stream. The present invention is particularly effective for removing organic solvents remaining in the β-form tris-(2,3-epoxypropyl)-isocyanurate crystals.

The entire disclosure of Japanese Patent Application No. 2000-047110 filed on Feb. 24, 2000, including specification, claims and summary are incorporated herein by reference in its entirety.

What is claimed is:

1. A method for reducing the amount of volatile organic liquids remaining in tris-(2,3-epoxypropyl)-isocyanurate crystals, which comprises pulverizing crystal particles of tris-(2,3-epoxypropyl)-isocyanurate obtained by a recrystallization method, while evaporating a volatile component from the surface of the particles.

2. The method for reducing the remaining volatile organic liquids according to claim 1, wherein the crystal particles of tris-(2,3-epoxypropyl)-isocyanurate are obtained by reacting cyanuric acid with epichiorohydrin in the presence of a catalyst to form a chiorohydrin ester of isocyanuric acid, followed by dehydrochlorination with an alkali, separating the resulting alkali metal chloride to obtain a reaction solution containing tris-(2,3-epoxypropyl)-isocyanurate, removing a solvent from the solution to obtain tris-(2,3-epoxypropyl)-isocyanurate, and recrystallizing it by means of a solvent.

3. The method for reducing the remaining volatile organic liquids according to claim 1, wherein a solvent for recrystallization solvent is selected from the group consisting of acetonitrile, dichloroethane, dioxane, toluene, dimethylformamide, methanol, ethanol and isopropyl alcohol.

4. A method for reducing the amount of volatile organic liquids remaining in tris-(2,3-epoxypropyl)-isocyanurate crystals, which comprises pulverizing crystal particles of tris- (2,3-epoxypropyl)-isocyanurate obtained by a recrystallization method, while evaporating a volatile component from the surface of the particles, wherein the pulverization while evaporating a volatile component from the surface of the particles is carried out in a gas stream.

5. The method for reducing the remaining volatile organic liquids according to claim 1, wherein the crystal particles are pulverized to an average particle size of from 0.5 to 20 μm.

6. A method for reducing the amount of volatile organic liquids remaining in tris-(2,3-epoxypropyl)-isocyanurate crystals, which comprises pulverizing crystal particles of tris-(2,3-epoxypropyl)-isocyanurate obtained by a recrystallization method, while evaporating a volatile component from the surface of the particles, wherein the concentration of the remaining volatile organic liquids is at most 300 ppm.

7. The method for reducing the remaining volatile organic liquids according to claim 1, wherein the crystal particles of tris-(2,3-epoxypropyl)-isocyanurate are crystal particles of β-form tris-(2,3-epoxypropyl)-isocyanurate.

8. The method for reducing the remaining volatile organic liquids according to claim 7, wherein a solvent for recrystallization solvent is selected from the group consisting of acetonitrile, dichloroethane, dioxane, toluene and dimethylformamide.

9. The method for reducing the remaining volatile organic liquids according to claim 1, wherein the remaining volatile organic liquids are epichlorohydrin and acetonitrile.

10. The method for reducing the remaining volatile organic liquids according to claim 4, wherein the crystal particles of tris-(2,3-epoxypropyl)-isocyanurate are obtained by reacting cyanuric acid with epicliiorohydrin in the presence of a catalyst to form a chiorohydrin ester of isocyanuric acid, followed by dehydrochlorination with an alkali, separating the resulting alkali metal chloride to obtain a reaction solution containing tris-(2,3-epoxypropyl)-isocyanurate, removing a solvent from the solution to obtain tris-(2,3-epoxypropyl)-isocyanurate, and recrystallizing it by means of a solvent.

11. The method for reducing the remaining volatile organic liquids according to claim 4, wherein a solvent for recrystallization solvent is selected from the group consisting of acetonitrile, dichloroethane, dioxane, toluene, dimethylformamide, methanol, ethanol and isopropyl alcohol.

12. The method for reducing the remaining volatile organic liquids according to claim 4, wherein the crystal particles are pulverized to an average particle size of from 0.5 to 20 μm.

13. The method for reducing the remaining volatile organic liquids according to claim 4, wherein the concentration of the remaining volatile organic liquids is at most 300 ppm.

14. The method for reducing the remaining volatile organic liquids according to claim 4, wherein the crystal particles of tris-(2,3-epoxypropyl)-isocyanurate are crystal particles of n-form tris-(2,3-epoxypropyl)-isocyanurate.

15. The method for reducing the remaining volatile organic liquids according to claim 4, wherein a solvent for recrystallization solvent is selected from the group consisting of acetonitrile, dichloroethane, dioxane, toluene and dimethylformamide.

16. The method for reducing the remaining volatile organic liquids according to claim 4, wherein the remaining volatile organic liquids are epichlorohydrin and acetonitrile.

17. The method for reducing the remaining volatile organic liquids according to claim 6, wherein the crystal particles of tris-(2,3-epoxypropyl)-isocyanurate are obtained by reacting cyanuric acid with epichlorohydrin in the presence of a catalyst to form a chlorohydrin ester of isocyanuric acid, followed by dehydrochlorination with an alkali, separating the resulting alkali metal chloride to obtain a reaction solution containing tris-(2,3-epoxypropyl)-isocyanurate, removing a solvent from the solution to obtain tris-(2,3-epoxypropyl)-isocyanurate, and recrystallizing it by means of a solvent.

18. The method for reducing the remaining volatile organic liquids according to claim 6, wherein a solvent for recrystallization solvent is selected from the group consisting of acetonitrile, dichioroethane, dioxane, toluene, dimethylformamide, methanol, ethanol and isopropyl alcohol.

19. The method for reducing the remaining volatile organic liquids according to claim 6, wherein the pulverization while evaporating a volatile component from the surface of the particles is carried out in a gas stream.

20. The method for reducing the remaining organic solvents according to claim 6, wherein the crystal particles are pulverized to an average particle size of from 0.5 to 20 μm.

21. The method for reducing the remaining volatile organic liquids according to claim 6, wherein the crystal particles of tris-(2,3-epoxypropyl)-isocyanurate are crystal particles of β-form tris-(2,3-epoxypropyl)-isocyanurate.

22. The method for reducing the remaining volatile organic liquids according to claim 6, wherein a solvent for recrystallization solvent is selected from the group consisting of acetonitrile, dichloroethane, dioxane, toluene and dimethylformamide.

23. The method for reducing the remaining volatile organic liquids according to claim 6, wherein the remaining volatile organic liquids are epichlorohydrin and acetonitrile.

* * * * *

UNITED STATES PATENT AND TRADEMARK OFFICE
CERTIFICATE OF CORRECTION

PATENT NO.    : 6,605,718 B2
DATED         : August 12, 2003
INVENTOR(S)   : Hisao Ikeda et al.

It is certified that error appears in the above-identified patent and that said Letters Patent is hereby corrected as shown below:

Column 16,
Line 19, "particle of n-form" should read -- particles of $\beta$-form --.

Signed and Sealed this

Thirtieth Day of December, 2003

JAMES E. ROGAN
*Director of the United States Patent and Trademark Office*